(12) United States Patent
Muller et al.

(10) Patent No.: US 12,311,089 B2
(45) Date of Patent: May 27, 2025

(54) MULTI-FUNCTIONAL PERITONEAL DIALYSIS MOBILE CART

(71) Applicants: BAXTER INTERNATIONAL INC., Deerfield, IL (US); BAXTER HEALTHCARE SA, Glattpark (CH)

(72) Inventors: Matthew Muller, Lindenhurst, IL (US); Tom Westberg, Lake Forest, IL (US); James W. Kendall, Mount Prospect, IL (US); Carlos Corrales, Vernon Hills, IL (US); Michela Carpani, San Felice sul Panaro (IT); Paolo Rovatti, Finale Emilia (IT); Luca Vinci, Poggio Rusco (IT); Mauro Suffritti, Medolla (IT)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 927 days.

(21) Appl. No.: 17/331,158

(22) Filed: May 26, 2021

(65) Prior Publication Data
US 2021/0369932 A1 Dec. 2, 2021

Related U.S. Application Data

(60) Provisional application No. 63/030,502, filed on May 27, 2020.

(51) Int. Cl.
*A61M 1/28* (2006.01)
*A61L 2/10* (2006.01)
(Continued)

(52) U.S. Cl.
CPC ............. *A61M 1/282* (2014.02); *A61L 2/10* (2013.01); *A61L 2/202* (2013.01); *A61L 2/26* (2013.01);
(Continued)

(58) Field of Classification Search
CPC .... A61M 1/159; A61M 1/1664; A61M 1/169; A61M 1/28; A61M 1/282; A61M 2202/0216; A61M 2205/12; A61M 2205/15; A61M 2205/3317; A61M 2205/3327; A61M 2205/3331;
(Continued)

(56) References Cited

U.S. PATENT DOCUMENTS

2012/0067805 A1* 3/2012 Childers ............... A61M 1/159
210/232
2020/0061273 A1* 2/2020 Hogard ............... A61M 1/1656

FOREIGN PATENT DOCUMENTS

CN 107648693 A * 2/2018

OTHER PUBLICATIONS

English translation copy of CN 107648693 A (2018).*

* cited by examiner

*Primary Examiner* — John Kim
(74) *Attorney, Agent, or Firm* — K&L Gates LLP

(57) ABSTRACT

A mobile dialysis therapy cart includes a top shelf; a cycler compartment positioned below the top shelf, the cycler compartment sized and shaped to house an APD cycler; a fluid bag management compartment sized and shaped to house at least two fluid bags; a drain compartment positioned below the fluid bag management compartment; and a plurality of wheels. The cart may include a heating device associated with the fluid bag management compartment and/or a sanitizing light source for sanitizing a location of a disposable set associated with the fluid bags.

19 Claims, 7 Drawing Sheets

(51) Int. Cl.
*A61L 2/20* (2006.01)
*A61L 2/26* (2006.01)
*A61M 1/14* (2006.01)
*A61M 1/16* (2006.01)

(52) U.S. Cl.
CPC .......... *A61M 1/159* (2022.05); *A61M 1/1664* (2014.02); *A61M 1/169* (2013.01); *A61M 1/28* (2013.01); *A61L 2202/11* (2013.01); *A61L 2202/16* (2013.01); *A61L 2202/24* (2013.01); *A61M 2202/0216* (2013.01); *A61M 2205/12* (2013.01); *A61M 2205/15* (2013.01); *A61M 2205/3317* (2013.01); *A61M 2205/3327* (2013.01); *A61M 2205/3331* (2013.01); *A61M 2205/3368* (2013.01); *A61M 2205/3379* (2013.01); *A61M 2205/3653* (2013.01); *A61M 2205/3686* (2013.01); *A61M 2205/8206* (2013.01); *A61M 2209/084* (2013.01)

(58) Field of Classification Search
CPC .. A61M 2205/3368; A61M 2205/3379; A61M 2205/3653; A61M 2205/3686; A61M 2205/8206; A61M 2209/084; A61L 2/10; A61L 2/202; A61L 2/26; A61L 2202/11; A61L 2202/16; A61L 2202/24
See application file for complete search history.

MULTI-FUNCTIONAL PERITONEAL DIALYSIS MOBILE CART

RELATED APPLICATIONS

This application claims the benefit of and priority to U.S. Provisional Patent Application No. 63/030,502 filed May 27, 2020, entitled "MULTI-FUNCTIONAL PERITONEAL DIALYSIS MOBILE CART", which is incorporated herein by reference in its entirety.

BACKGROUND

The present disclosure relates generally to medical fluid treatments and in particular to dialysis fluid treatments. Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HDF, and HF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two- or three-days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated over a dialysis session, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to be drained from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, through the catheter, into the drain. As with the manual process, several drain, fill and dwell cycles occur during dialysis. A "last fill" may occur at the end of the APD treatment. The last fill fluid may remain in the peritoneal chamber of the patient until the start of the next treatment or may be manually emptied at some point during the day.

In any of the above modalities using an automated machine, the automated machine operates typically with a disposable set, which is discarded after a single use. Daily disposables require space for storage, which can become a nuisance for home owners and businesses. Setting up and organizing an APD therapy involves sanitizing work surfaces, un-packaging and positioning various components (e.g., dialysis solution bags and drain bags) about the APD machine, heating dialysis solution bags, connecting bags, etc. Moreover, daily disposable replacement requires daily setup time and effort by the patient or caregiver at home or at a clinic.

There is also a need for APD devices to be mobile so that the patient may easily transport the various components for the APD therapy in an organized manner. Additionally, there is a need for APD devices and components to be mobile such that the patient may bring his or her device on vacation or for work travel.

For each of the above reasons, it is desirable to provide an improved structure and associated functionality for organizing and performing an APD therapy.

SUMMARY

The present disclosure relates to a multi-function mobile cart to house, organize, and improve the ease of use of an automated peritoneal dialysis ("APD") system. In general, the APD system may employ an APD machine or cycler that operates a disposable set.

In light of the disclosure herein and without limiting the disclosure in any way, in a first aspect of the present disclosure, which may be combined with any other aspect listed herein unless specified otherwise, a mobile dialysis therapy cart includes a top shelf, a cycler compartment positioned below the top shelf, a fluid bag management compartment, a drain compartment. The cycler compartment is sized and shaped to house an automated peritoneal dialysis ("APD") cycler. The fluid bag management compartment is sized and shaped to house at least two fluid bags. The drain compartment is positioned below the fluid bag management compartment. The mobile dialysis therapy cart may also include a plurality of wheels.

In a second aspect of the present disclosure, which may be combined with any other aspect listed herein unless specified otherwise, the mobile dialysis therapy cart includes at least one sanitizing device configured to sanitize at least one location of a disposable set associated with the fluid bags.

In a third aspect of the present disclosure, which may be combined with any other aspect listed herein unless specified otherwise, the sanitizing device includes a sanitizing light source directed towards the location.

In a fourth aspect of the present disclosure, which may be combined with any other aspect listed herein unless specified otherwise, the sanitizing device includes an ozone generator configured to direct ozone containing gas towards the location.

In a fifth aspect of the present disclosure, which may be combined with any other aspect listed herein unless specified otherwise, the fluid bag management compartment includes a heating device adapted to heat dialysis fluid in one or more fluid bags positioned within the fluid bag management compartment.

In a sixth aspect of the present disclosure, which may be combined with any other aspect listed herein unless specified otherwise, the heating device includes at least one of a resistive plate heater, an inductive heater, and a micro-wave heater.

In a seventh aspect of the present disclosure, which may be combined with any other aspect listed herein unless specified otherwise, the top shelf includes a hinge configured to enable a portion of the top shelf to rotate upwards to provide access to the cycler compartment.

In an eighth aspect of the present disclosure, which may be combined with any other aspect listed herein unless specified otherwise, the mobile dialysis therapy cart includes a drain trolley housed within the drain compartment. Additionally, the drain compartment may include a ramp for the drain trolley.

In a ninth aspect of the present disclosure, which may be combined with any other aspect listed herein unless specified otherwise, the fluid bag management compartment includes at least two telescoping sub-shelves configured to collapse.

In a tenth aspect of the present disclosure, which may be combined with any other aspect listed herein unless specified otherwise, the mobile dialysis therapy cart includes at least one of a urea sensor, a creatinine sensor, a conductivity sensor, a turbidity sensor for sensing patient effluent or a fluid presence sensor for detecting a leak in the fluid bag management compartment.

In an eleventh aspect of the present disclosure, which may be combined with any other aspect listed herein unless specified otherwise, the mobile dialysis therapy cart includes at least one of a pressure sensor, a contact sensor, a strain sensor or a load or weight sensor for sensing a mass or volume of fluid that is delivered to or from the patient.

In a twelfth aspect of the present disclosure, which may be combined with any other aspect listed herein unless specified otherwise, the mobile dialysis therapy cart includes a level sensor for sensing an orientation of the cart, the cycler compartment, the fluid bag management compartment, or the drain compartment.

In a thirteenth aspect of the present disclosure, which may be combined with any other aspect listed herein unless specified otherwise, the drain compartment includes at least one of a pressure sensor, a contact sensor, a strain sensor, a load or weight sensor, a urea sensor, a creatinine sensor, a turbidity sensor or a proximity sensor.

In a fourteenth aspect of the present disclosure, which may be combined with any other aspect listed herein unless specified otherwise, a mobile dialysis therapy cart includes a top shelf, a fluid bag management compartment, at least one temperature sensor, and a control unit. The fluid bag management compartment is be located beneath the top shelf. Additionally, the fluid management compartment is heated and includes at least one heating device for heating a plurality of fluid bags. The at least one temperature sensor is located to sense a temperature associated with dialysis fluid located within the plurality of fluid bags. The control unit is associated with the heating device and the at least one temperature sensor. The control unit is programmed to use an output from the at least one temperature sensor to operate the heating device to heat dialysis fluid within the plurality of fluid bags to a desired temperature.

In a fifteenth aspect of the present disclosure, which may be combined with any other aspect listed herein unless specified otherwise, the mobile dialysis therapy cart includes a drain compartment, which may be positioned below the fluid bag management compartment.

In a sixteenth aspect of the present disclosure, which may be combined with any other aspect listed herein unless specified otherwise, the mobile dialysis therapy cart includes at least one effluent sensor associated with the drain compartment.

In a seventeenth aspect of the present disclosure, which may be combined with any other aspect listed herein unless specified otherwise, the mobile dialysis therapy cart includes a cycler compartment positioned below the top shelf. The cycler compartment may be sized and shaped to house an APD cycler.

In an eighteenth aspect of the present disclosure, which may be combined with any other aspect listed herein unless specified otherwise, the mobile dialysis therapy cart includes at least one sanitizing device. The sanitizing device may be a sanitizing light source associated with at least one of the fluid bag management compartment or the cycler compartment.

In a nineteenth aspect of the present disclosure, which may be combined with any other aspect listed herein unless specified otherwise, a mobile dialysis therapy cart includes a top shelf, a cycler compartment, a plurality of fluid bag hooks, and a drain compartment. The mobile dialysis therapy cart may also include a plurality of wheels. The cycler compartment is positioned below the top shelf. Additionally, the cycler compartment is sized and shaped to house an APD cycler.

In a twentieth aspect of the present disclosure, which may be combined with any other aspect listed herein unless specified otherwise, the mobile dialysis therapy cart includes at least one sanitizing device configured to sanitize a location of at least one fluid bag held by the at least one fluid bag hook.

In a twenty-first aspect of the present disclosure, which may be combined with any other aspect listed herein unless specified otherwise, the sanitizing device includes a sanitizing light source directed toward the location of the at least one fluid bag.

In a twenty-second aspect of the present disclosure, which may be combined with any other aspect listed herein unless specified otherwise, the top shelf includes a hinge configured to enable a portion of the top shelf to rotate upwards and fold over itself to provide access to the cycler compartment.

In a twenty-third aspect of the present disclosure, which may be combined with any other aspect listed herein unless specified otherwise, the mobile dialysis therapy cart includes a drain trolley housed within the drain compartment. The drain compartment includes a door, and the door is configured to fold down away from the drain compartment to provide a ramp for the drain trolley.

In a twenty-fourth aspect of the present disclosure, which may be combined with any other aspect listed herein unless specified otherwise, the mobile dialysis therapy cart includes at least one of a urea sensor, a creatinine sensor, and a turbidity sensor associated with the drain compartment.

In a twenty-fourth aspect of the present disclosure, which may be combined with any other aspect listed herein unless specified otherwise, a mobile dialysis therapy cart includes a top shelf, a cycler compartment, a fluid bag management compartment, and a drain compartment. The mobile dialysis therapy cart may also include a plurality of wheels. The top shelf includes a top surface. Additionally, the top shelf is adjustable and the top surface is hinged. The cycler compartment is positioned below the top shelf, and the cycler compartment is adjustable and is sized and shaped to house an APD cycler. The fluid bag management compartment includes at least two telescopic sub-shelves. Each of the at least two telescopic sub-shelves are sized and shaped to support a fluid bag. The drain compartment is positioned below the fluid bag management compartment. Additionally, the drain compartment includes a door that is adapted to open from the top and fold down towards a bottom of the dialysis therapy cart. The door may serve as a ramp surface for a drain trolley housed in the drain compartment.

In a twenty-sixth aspect of the present disclosure, which may be combined with any other aspect listed herein unless specified otherwise, the mobile dialysis therapy cart includes a display device that is removable from the cart while maintaining connectivity with the cart.

In a twenty-seventh aspect of the present disclosure, which may be combined with any other aspect listed herein unless specified otherwise, the mobile dialysis therapy cart includes at least one of a urea sensor, a creatinine sensor, a conductivity sensor, and a turbidity sensor associated with the drain compartment.

In a twenty-eighth aspect of the present disclosure, which may be combined with any other aspect listed herein unless specified otherwise, a dialysis therapy system includes a cart, an APD cycler, and at least two fluid bags. The cart includes a top shelf, a cycler compartment positioned below the top shelf, a fluid bag management compartment, and a plurality of wheels. The APD cycler is housed within the cycler compartment, which is sized and shaped to house the APD cycler. The at least two fluid bags are housed within the fluid bag management compartment, which is sized and shaped to house at least two fluid bags.

In a twenty-ninth aspect of the present disclosure, which may be combined with any other aspect listed herein unless specified otherwise, the cart includes a drain compartment positioned below the fluid bag management compartment.

In a thirtieth aspect of the present disclosure, which may be combined with any other aspect listed herein unless specified otherwise, the dialysis therapy system includes a drain bag. The drain bag may be housed within the drain compartment.

In a thirty-first aspect of the present disclosure, which may be combined with any other aspect listed herein unless specified otherwise, the dialysis therapy system includes at least one of a urea sensor, a creatinine sensor, and a turbidity sensor associated with the drain bag or the drain compartment.

In a thirty-second aspect of the present disclosure, which may be combined with any other aspect listed herein unless specified otherwise, the dialysis therapy system includes a sanitizing device configured to sanitize a portion of the dialysis therapy system.

In a thirty-third aspect of the present disclosure, which may be combined with any other aspect listed herein unless specified otherwise, the sanitizing device is at least one of a sanitizing light source or an ozone generator.

In a thirty-fourth aspect of the present disclosure, which may be combined with any other aspect listed herein unless specified otherwise, the dialysis therapy system includes at least one of a load or weight sensor, a pressure sensor, a strain sensor, and a level sensor.

In a thirty-fifth aspect of the present disclosure, which may be combined with any other aspect listed herein unless specified otherwise, any of the features, functionality and alternatives described in connection with any one or more of FIGS. 1 to 4 may be combined with any of the features, functionality and alternatives described in connection with any other of FIGS. 1 to 4.

It is accordingly an advantage of the present disclosure to provide a mobile cart with a compact footprint to reduce the space required to conduct an APD treatment in a patient's room.

It is another advantage of the present disclosure to provide a mobile cart that allows a patient to move APD therapy equipment to different rooms and locations and to improve patient mobility during treatment.

It is yet another advantage of the present disclosure to provide a multi-function cart that organizes components for APD therapy.

It is a further advantage of the present disclosure to provide a cart capable of heating and maintaining the temperature of multiple dialysis solution bags.

It is yet a further advantage of the present disclosure to provide an easily removable and mobile drain bag trolley for final wasting of effluent fluid.

It is yet another advantage of the present disclosure to provide a multi-function cart that is configurable to enable optimal use and organization for varied bedroom environments.

It is a further advantage of the present disclosure to provide a cart that facilitates a repeatable set-up procedure with common locations for therapy components to reduce error and optimize instrument operation.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
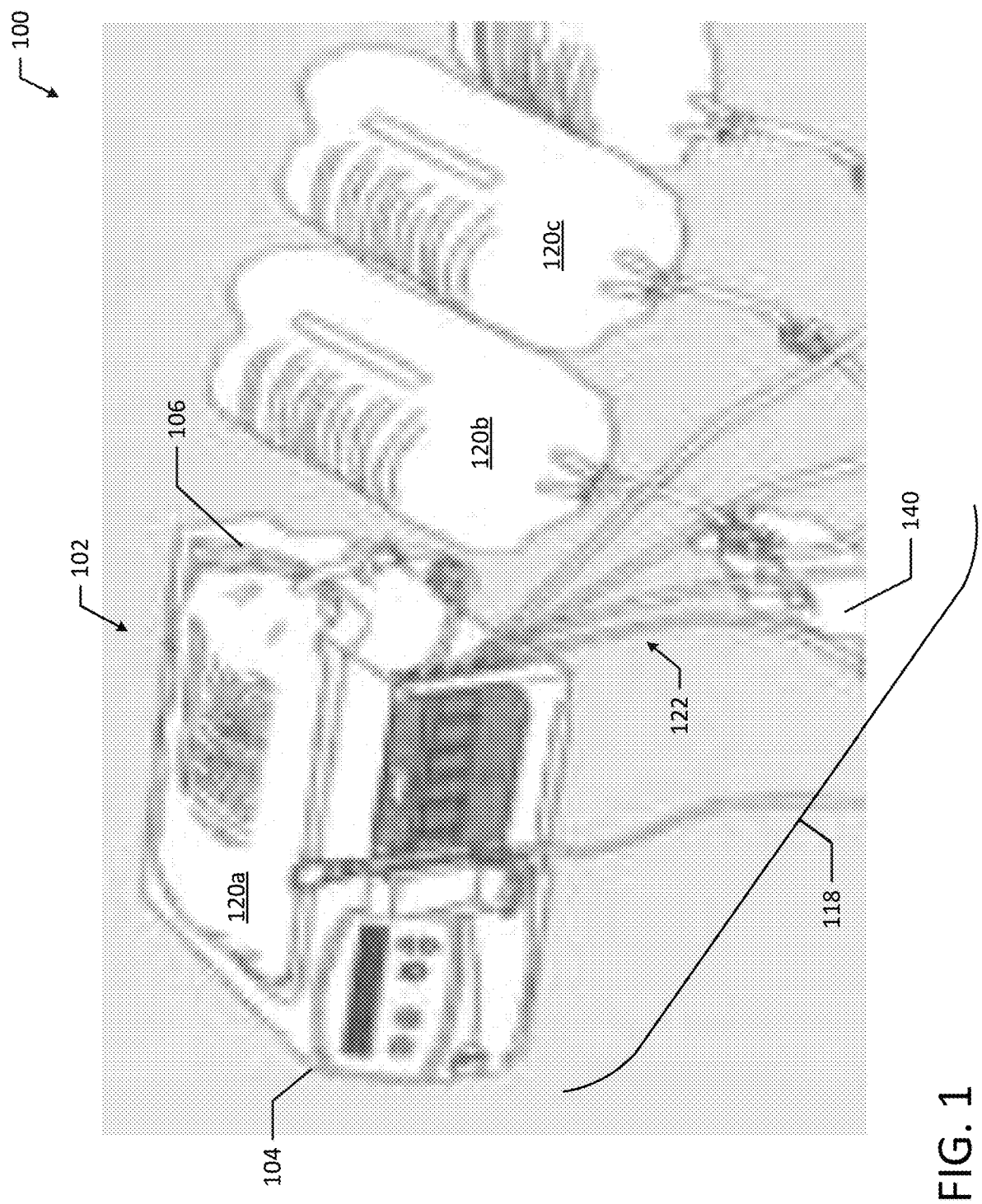
FIG. 1 is a perspective view of an automated peritoneal dialysis ("APD") machine operating with a disposable, fluid carrying set.

Referring now to the drawings and in particular to FIG. 1, a typical configuration 100 for an automated peritoneal dialysis ("APD") system 102 includes and APD machine or cycler 104 that operates with a disposable set 118 including a disposable cassette (located within cycler 104), fluid containers or bags 120a to 120c and associated lines or tubing 122. The fluid containers or bags 120a to 120c may be dialysis fluid bags, dialysis solution bags, heating bags, solution bags, concentrate bags, etc. and may be commonly and generally referred to herein as fluid bags 120. APD machine or cycler 104 in the illustrated embodiment includes a heating tray 106 atop the APD machine or cycler 104. During setup regarding cycler 104 and disposable set 118, a patient may implement "ad hoc" solutions to organize and position the various components required to perform an APD therapy. For example, the patient typically has to find space to unpack the various fluid bags 120a to 120c and lines 122 and place them somewhere near APD machine 104.

Specifically, a patient may place a fluid bag 120a (e.g., dialysis solution or heating bag) on the heater or heating tray 106. Then, the patient may position other fluid bags 120b, c (e.g., dialysis solution bags) near the APD machine or cycler 104 for connection to the disposable cassette. For example, each evening, the patient may set up the APD machine or cycler 104 to perform three to five fluid treatment exchanges. To perform three to five exchanges, the patient may connect three to five fluid bags 120a to c (e.g., dialysis solution bags) to the disposable cassette operating with the cycler 104. A heating source, such as the cycler's 104 heating tray 106 may warm the fresh dialysis solution before it enters the patient's body. Additionally, the patient may position a drain bag 140 near the APD machine or cycler 104 to check drain fluid turbidity.

Implementing "ad hoc" solutions to organize and position the various components required to perform the APD therapy creates stress and discomfort and poses a sanitary risk for patients. For example, a patient's room may provide inadequate space for preparation and organization of a therapy treatment. Additionally, the portions of the patient's room that are used as an "ad hoc" solution should be manually cleaned each day prior to treatment setup, which is burdensome to the patient. Improper loading of the fluid bag 120a (e.g., dialysis solution or heating bag), for example, may lead to only portions of the dialysis fluid volume being heated at a time, causing delays and time loss waiting for dialysis solution to warm to an appropriate temperature before entering the patient's body.

In addition, a PD patient typically has lower mobility and flexibility due to the mobility constraints created by the "ad hoc" solutions. For example, the repositioning of the cycler 104 may be limited by the length of the cycler's 104 power cord and/or by the physical location of the cycler 104 and of the fluid bags 120 (e.g., dialysis solution bags and drain bag 140 placed onto small furniture such as a small chair, table or nightstand in the patient's bedroom). Even though each of the components for an APD therapy is independently portable (e.g., the cycler 104, fluid bags 120 and drain bag 140), the components together drastically constrain movement. The patient's traveling capabilities with "ad hoc" solutions are also limited due to the combined mobility constraints created by the components, for example, which may require cleaning of the various surfaces at the new location, lifting and carrying each component (e.g., cycler 104, fluid bags 120, drain bag 140, etc.) to the new location, etc.

Figure 2B:
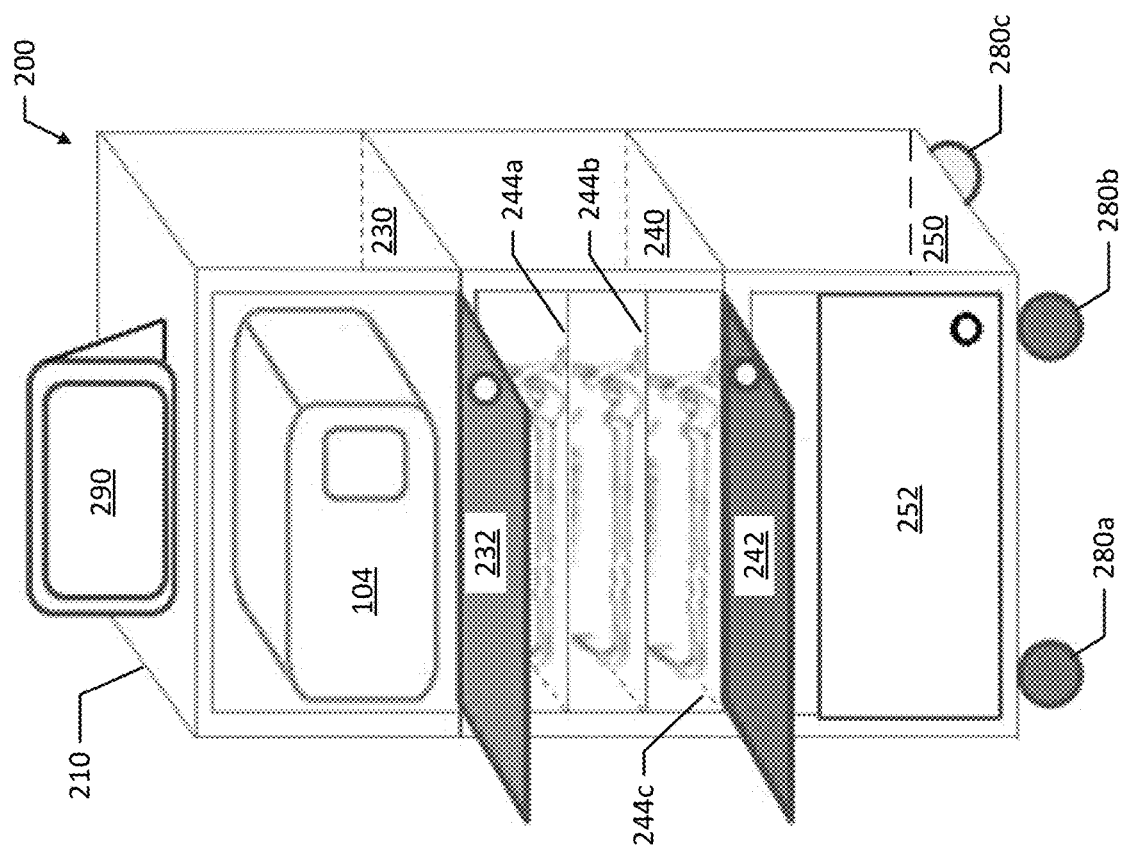
FIGS. 2A, 2B and 2C are perspective views of a first embodiment for a mobile cart of the present disclosure.
Figure 2A:
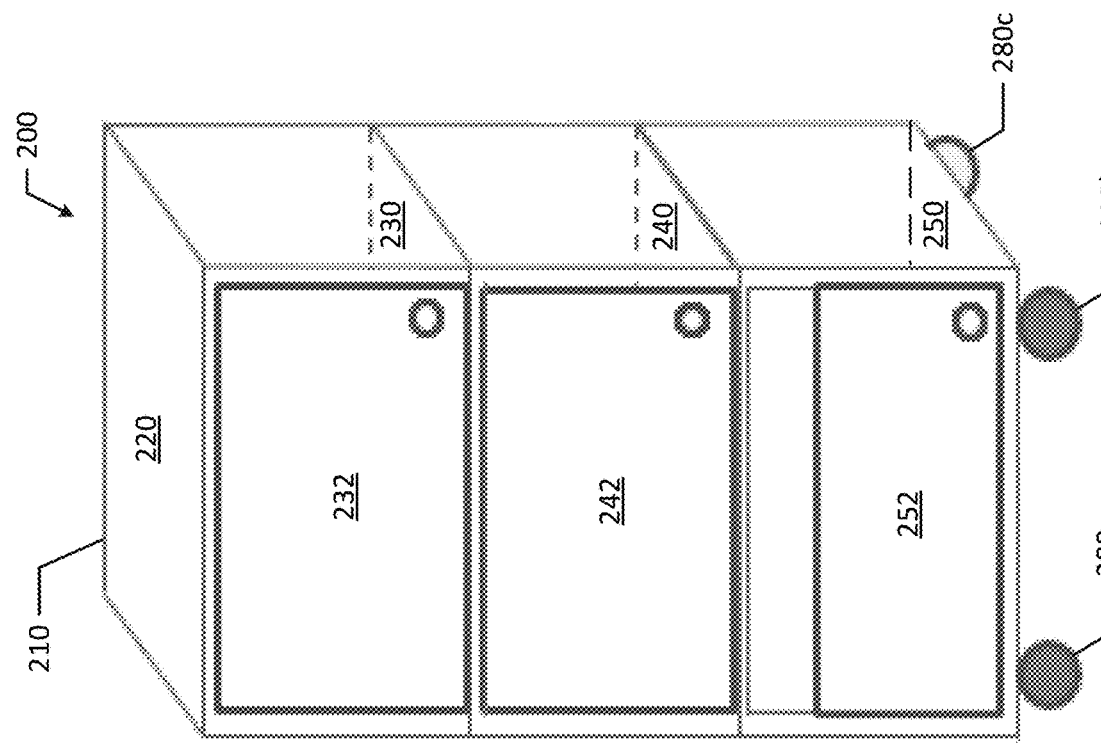
Figure 2C:
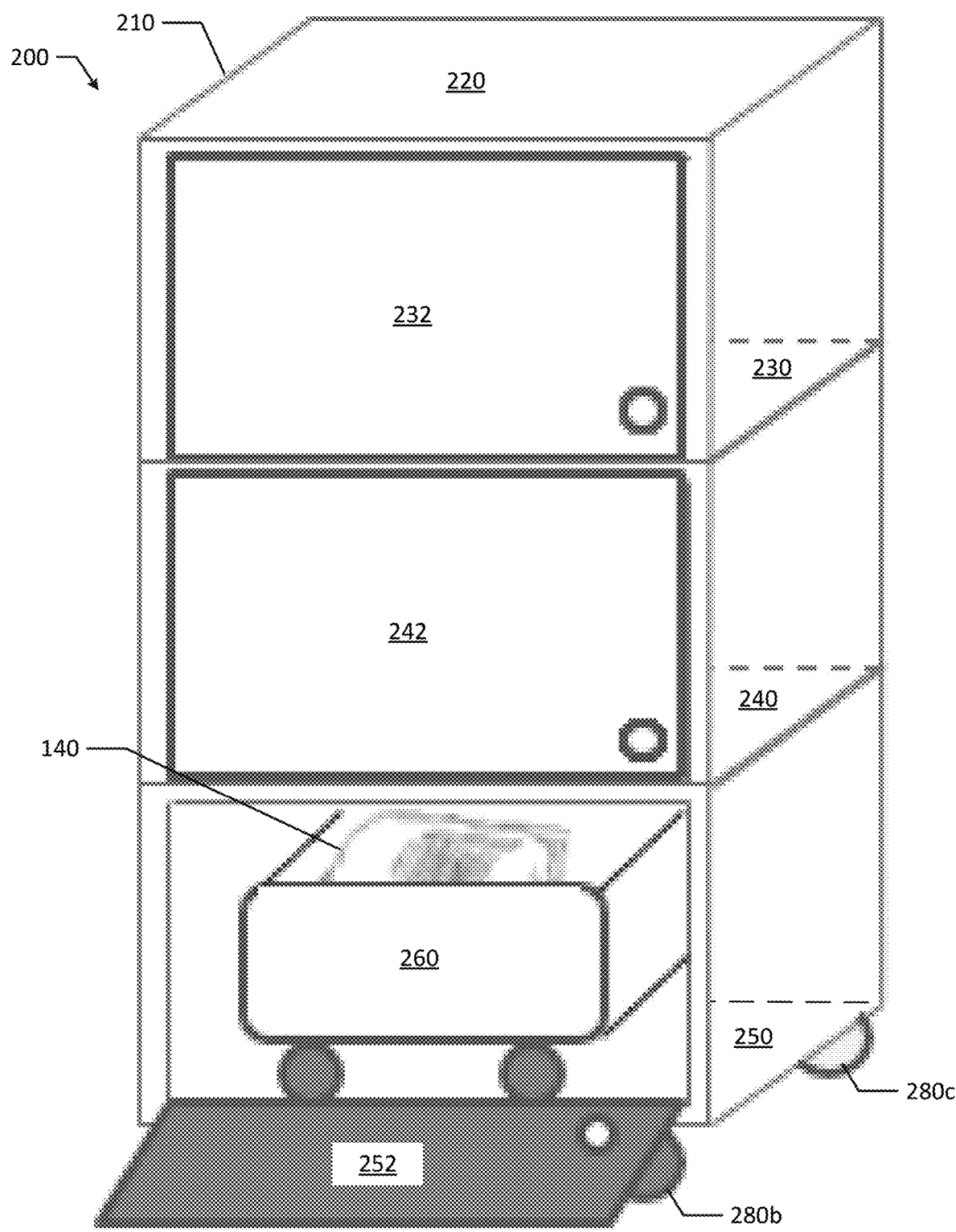

FIGS. 2A to 2C illustrate an APD therapy management system 200 that includes a cart 210, which allows the system 200 to be moved readily, e.g., from a family room to a bedroom and vice versa. The cart 210 may be a mobile cart and/or a multi-function cart, and/or a medical therapy cart, such as a dialysis therapy cart. For example, cart 210 may include wheels 280a to 280d that allow cart 210 to be moved from one room to another in the patient's house. During cleaning, cart 210 may be moved to a kitchen or utility room in which cleaning supplies are readily accessible. Additionally, the mobility of cart 210 allows the cart 210 to be rotated or positioned in a preferred direction of operation (e.g., facing patient's bed). One or more handle (not pictured) may be provided to facilitate the movement of the cart 210. In one embodiment, the handle may be rotated out of the way (e.g., upwardly or downwardly) when not needed.

Wheels 280a to 280d, hereinafter referred to generally as wheels 280, may be casters or rollers that enable cart 210 to be pushed along flat surfaces. Additionally, wheels 280 may be sized such that cart 210 can move along carpet and over other small obstacles. Each of the wheels 280 may rotate independently of the others, and around both horizontal and vertical axis, to provide improved turning and cart mobility in tight spaces. Cart 210 may include three, four, or more wheels 280. Additionally, wheels 280 may include stops or brakes to prevent or limit further movement once the cart 210 is moved to a desired location.

Cart 210 may be powered via AC power and/or battery power. For example, cart 210 may include a battery (e.g., battery 415 of FIG. 4), which is used to provide the APD machine or cycler 104 with battery power when no AC power is available. For example, to move system 200, the patient may unplug a power cord and proceed to wheel cart 210 to any desired destination. Battery 415 may be a long-lasting battery powering the cycler 104, while allowing cart 210 to move to another room and avoiding the discontinuation of treatment while the patient moves. In an embodiment, battery 415 is a rechargeable battery, which is recharged while cart 210 is connected to AC power.

FIGS. 2A to 2C illustrate that cart 210 may include a top shelf 220, a cycler compartment 230, a fluid bag management compartment 240, and a drain compartment 250. Compartments 230, 240, 250 may be enclosures similar to a drawer or a lock-box with a door. In another example, compartments 230, 240, 250 include shelves that are open on at least one side. Compartments or shelves 220, 230, 240 and 250 may hold supplies needed for a dialysis therapy and organize each of the therapy components. For example, the compartments and shelves enable a patient to organize and route tubing from fluid bags 120 in fluid bag management compartment 240 that extend to the disposable cassette interfacing with the cycler 104 located in the cycler compartment 230. A patient tube leads from the disposable cassette in the cycler compartment 230 to the patient. A drain line leads from the disposable cassette in the cycler compartment 230 to the drain bag 140 located in the drain compartment 250.

Top shelf 220 and compartments 230, 240, 250 or shelves provide surfaces having enough stability to support therapy components housed in cart 210, which further protects the therapy components against accidental bumps and contacts. In an example, the compartments or shelves may be open from the front side of cart 210. FIG. 2A illustrates that one or more of the compartments or shelves 230, 240, 250 may include a respective door 232, 242, 252, which may be hinged doors.

Door(s) 232, 242, 252 may include respective locking mechanisms. The locking mechanisms maintain doors 232, 242, 252 in a closed position allowing the cart 210 to be transported and moved without any of the APD components falling out of the cart. The locking mechanisms may additionally securely store APD components and keep those components out of reach from children, pets, etc.

FIG. 2B illustrates that fluid bag management compartment 240 includes multiple slots or sub-shelves (e.g., sub-shelves 244a to 244c) that organize fluid bags 120 at the beginning of the treatment. In the illustrated example, fluid bag management compartment 240 includes three slots or sub-shelves 244a to 244c for three fluid bags 120 that serve to supply additional dialysis fluid for future treatment cycles. Additionally, another fluid bag 120a (e.g., heating bag) sits atop the cycler 104 in one embodiment. In other examples, fluid bag management compartment 240 may be configured to accommodate additional fluid bags 120, while fluid may take place without requiring the patient to place a bag or container atop the cycler 104.

In an example, each of the slots or sub-shelves 244a to 244c is telescopic or otherwise moveable, such that each shelf can collapse or move inward and out of the way when not used to support a fluid bag 120. The slots or sub-shelves 244a to 244c may alternatively or additionally be hinged and capable of folding out of the way (e.g., folding upwardly) to provide additional access to the shelf below. For example, the slot or sub-shelf 244a may telescopically collapse inward and/or fold upward and out of the way to provide additional access to the slot or sub-shelf 244b. In other examples, the slots or sub-shelves 244a to 244c may be telescoping, collapsed or folded out of the way to accommodate larger fluid bags. The slots or sub-shelves 244a to 244c may further alternatively or additionally be removable and placed for example on the bottom of cart 210.

Still further alternatively or additionally, fluid bag management compartment 240 and its associated slots or sub-shelves 244a to 244c may be sloped to orient each fluid bag so that the bag outlet port resides below the rest of the bag for optimum drainage and air handling. The sloped configuration of fluid bag management compartment 240 advantageously causes dialysis fluid to flow from the bags until emptied, leaving air free to migrate up towards the back of the bags and to remain trapped therein. Similarly, drain compartment 250 may also be sloped to assist with flow into or out of drain bag 150.

As shown specifically in FIG. 2B, APD machine or cycler 104 can, for example, be located within cycler compartment 104 or shelf 230 above fluid bag management compartment or shelf 240, which provides ready access to the slots or subshelve(s) 244a to 244c.

The cart 210 may also include a display device 290. The display device 290 may be integrated with or be a removable or separable from the cart 210. The display device 290 may be communicatively coupled to the cycler 104 and/or any of the sensors as discussed in more detail below for the presentation of information to the patient. For example, the display device 290 may present user interface information from the cycler 104 to the patient. The display device 290 may advantageously present information to the patient when the input devices and the display of cycler 104 is facing away from the patient. For example, a patient may be unable to position the cart 210 such that the input devices and display of the cycler 104 face the patient's bed. However, the patient may remove and reposition the display device 290 in a convenient location that is viewable by the patient even when the cycler 104 is out of sight.

As illustrated in FIG. 2C, the cart 210 accommodates drain bag 140, e.g., in drain compartment 250. The cart 210 may also include a drain trolley 260 for draining and transporting drain bag 140. The drain trolley 260 may be self-contained. If a drain line is run to a house drain instead of a drain bag 140, the drain line may be removed from the drain and placed in the drain compartment 250 (e.g., within drain trolley 260) when system 200 is moved. The drain trolley 260 allows for easy transport of drain bag 140 to a restroom for a final draining of effluent waste fluid, e.g., to a toilet or bathtub. The drain trolley 260 advantageously allows a patient to transport drain bag 140 without having to move the entire cart 210 into the restroom. In an example, a door 252 additionally serves as a ramp for trolley 260 to slide down from the bottom of the compartment to the floor or ground. The door 252 (along with other doors described herein) may be a front door. In other examples, a long drain tube may be incorporated into the drain compartment 250, which enables waste fluid to be drained without having to transport or empty a heavy drain bag 140.

Alternatively, cart 210 may include a drain line instead of a drain compartment 250 or drain trolley 260. For example, cart 210 may be positioned to drain fluid directly via a drain line without temporarily storing the fluid in drain compartment 250 or drain trolley 260. The drain line may be of sufficient length to allow a patient to directly drain effluent waste fluid in a toilet or a bathtub.

FIGS. 3A to 3F illustrate an alternate APD therapy management system 300, which includes alternative cart 310. The cart 310 may likewise be a mobile cart and/or a multi-function cart, and/or a medical therapy cart, such as a dialysis therapy cart. Cart 310 in the illustrated embodiment includes a top shelf 320, a cycler compartment or shelf 330, and a drain compartment or shelf 350. Similar to FIGS. 2A to 2C, compartments or shelves 330 and 350 may be or form compartments. Instead of placing the supply bags in a fluid bag management compartment or shelf 240 (illustrated in FIGS. 2A to 2C), the cart 310 in the illustrated embodiment includes a plurality of fluid bag fingers or hooks 340a to 340n, hereinafter referred to generally as fluid bag fingers or hooks 340 or simply as fingers or hooks 340. For example, a finger or hook 340 may support a fluid bag and may be described as a fluid bag hook; or the hook 340 may support a drain bag and may be described as a drain bag hook. In the embodiment illustrated in FIGS. 3A to 3D, the compartments or shelves are open from each side of the cart 310. The cart 310 is therefore configured to allow a patient or a caregiver to place hooks 340a to 340n along any one or more desired side of the cart 310.

Similar to cart 210, cart 310 may include wheels 380a to 380d, which allow cart 310 to be moved from one room to another in the patient's house or to be repositioned in a preferred orientation for operation (e.g., facing patient's bed). Positioning cart 210 or 310 in a preferred direction or orientation, such as facing the patient's bed, allows the input devices and the display of the cycler 104 to face the patient's bed while the patient falls asleep. Here, if an alarm sounds, the patient can access the cycler 104, the patient line, the fluid bags 120 and/or the associated lines, etc., without having to get out of bed. A handle (not pictured) may facilitate moving cart 310. In one embodiment, the handle may be rotated out of the way (e.g., upwardly or downwardly) when not needed. The patient may use the handle or otherwise turn cart 310 during treatment, e.g., while in bed, to access any desired area of the cart 310.

Wheels 380a to 380d, hereinafter referred to generally as wheels 380, may be casters or rollers that enable the cart 310 to be pushed along flat surfaces. Additionally, wheels 380 may be sized such that cart 310 may easily move along carpet and other small obstacles. Each of the wheels 380 may rotate independently of the others, and around both horizontal and vertical axis, to provide improved turning and cart mobility in tight spaces. Cart 310 may include three, four, or more wheels 380. Additionally, wheels 380 may include stops or brakes 382 to prevent or limit further movement once the cart 310 is in a desired location.

Figure 3B:
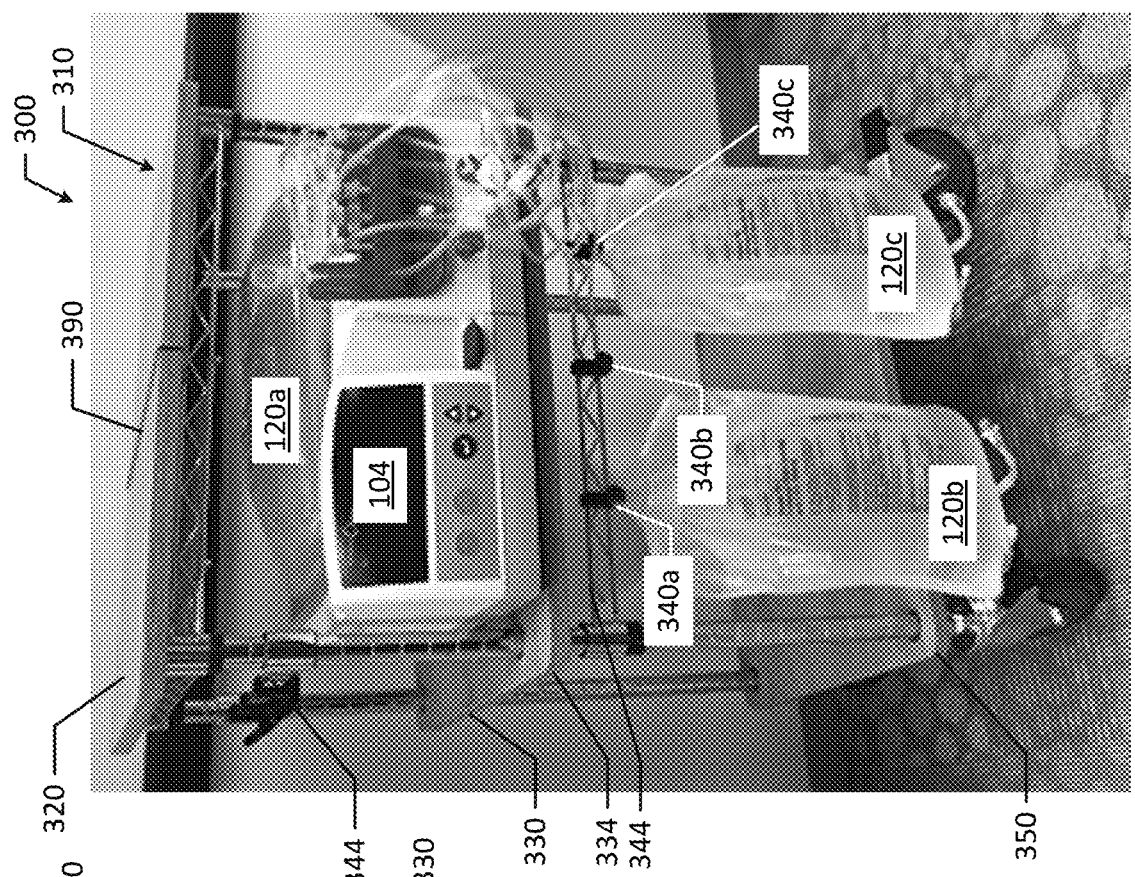
FIG. 3B is a front elevation view of the second embodiment for the mobile cart of the present disclosure.

Fingers or hooks 340 may be placed in various positions and configurations on the cart 310. As illustrated in FIG. 3B, the cart 310 may include rails 344. The rails 344 may provide mounting points for fingers or hooks 340. In an example, rails 344 may be adjustable such that the rails can be moved to different heights between compartments or shelves 320, 330 and 350. Rails 344 and thus fingers or hooks 340 are therefore capable of being placed on any side of the cart 310 to support fluid bags 120. Fluid bags 120 hanging from fingers or hooks 340 are oriented such that the bag outlet ports reside below the rest of the bag for optimum drainage and air handling, which advantageously causes dialysis fluid to flow from the fluid bags 120 until emptied, leaving air free to migrate up towards the top of the bags and to remain trapped therein.

Figure 3A:
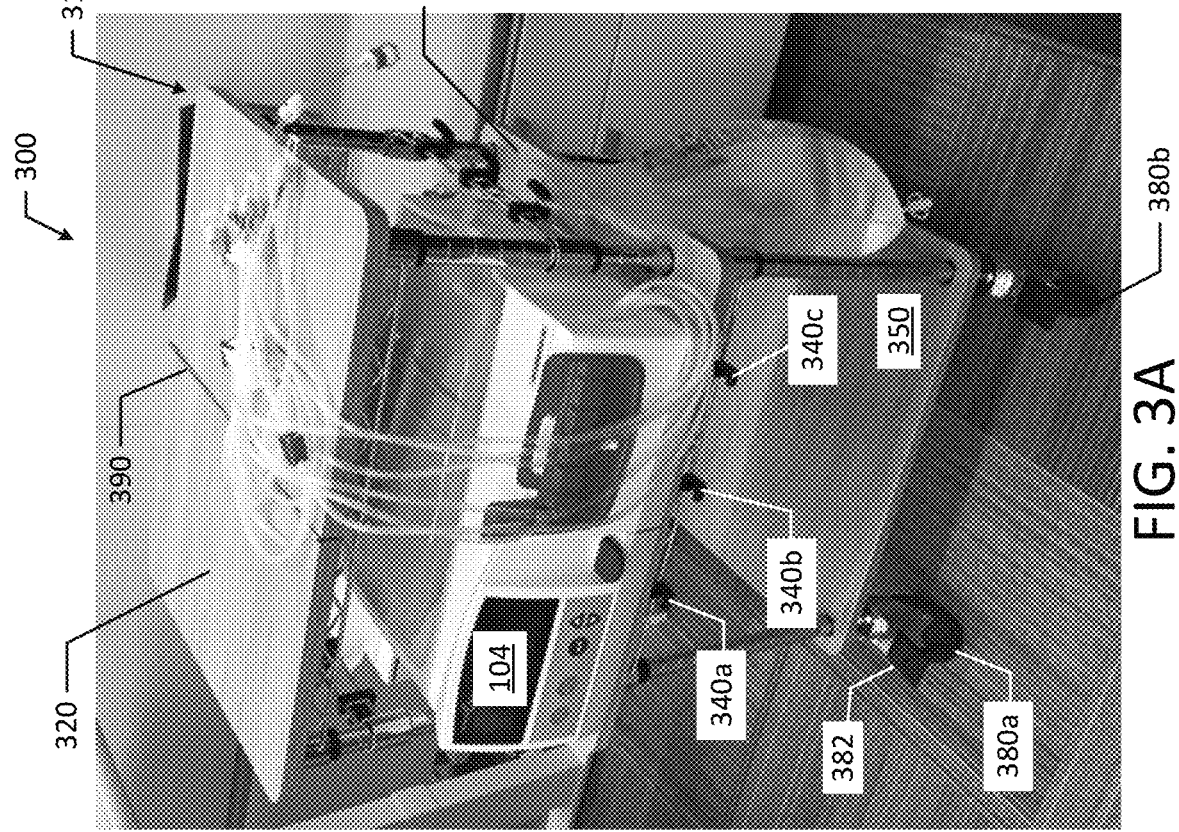
FIG. 3A is a perspective view of a second embodiment for a mobile cart of the present disclosure.

As discussed above, fluid bags 120a to 102c (e.g., dialysis solution bags 120) may be suspended on fingers or hooks 340 arranged about desired sides of the cart 310. For example, fingers or hooks 340 may be positioned on the side of the cart 310 as illustrated in FIG. 3A and/or along the front of the cart 310 as illustrated in FIG. 3B. In another example, fingers or hooks 340 are positioned along the top portion of a fluid bag management compartment (e.g., similar to fluid bag management compartment 240 of FIGS. 2A to 2C), which is sized and shaped to allow fluid bags 120 to hang within the compartment while also being contained within the cart 310. Alternatively or additionally, a dialysis solution or fluid bag 120 may sit inside a shallow concave depression forming the heating tray 106 atop the APD machine or cycler 104, which may be sized and shaped to accommodate a typical 5 liter bag of PD solution, for example.

Similar to cart 210, the various compartments, shelves, fingers or hooks of the cart 310 may hold any ancillary supplies needed for a dialysis therapy and to organize each of the supplies and therapy components. Carts 210 and 310 not only provide a means to optimally organize treatment, carts 210 and 310 also allow the patient to setup for a next treatment when tearing down a just-completed treatment, e.g., in the morning. In combination with the pre-setup, systems 200 and 300 allow the patient to pre-program a start time for the next treatment, so that the system 200 or 300 is fully primed and ready to commence in the day or evening.

Figure 3D:
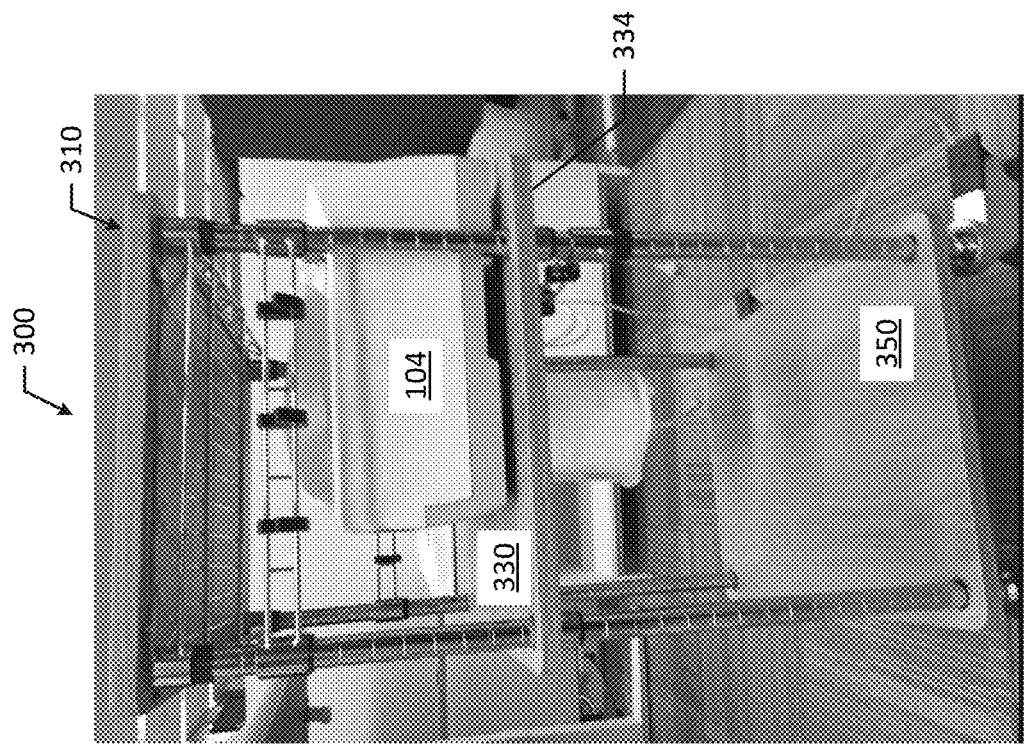
FIG. 3D is a side elevation view of the second embodiment for the mobile cart of the present disclosure.
Figure 3C:
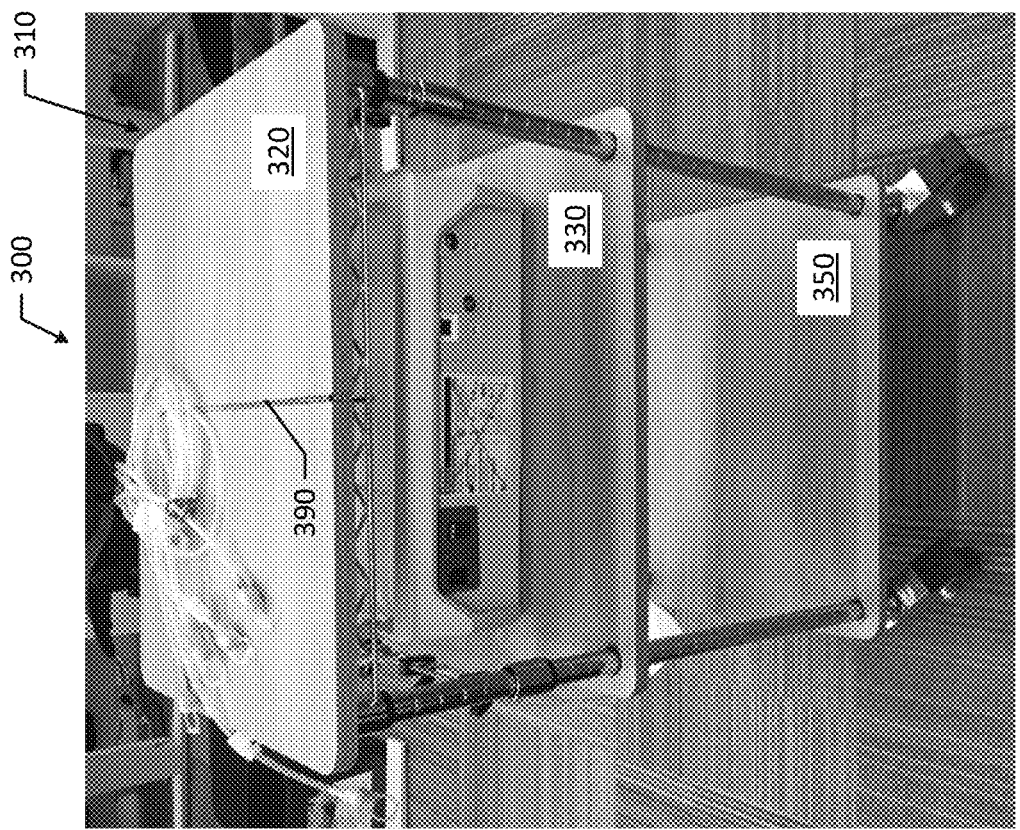
FIG. 3C is a rear elevation view of the second embodiment for the mobile cart of the present disclosure.
Figure 3E:
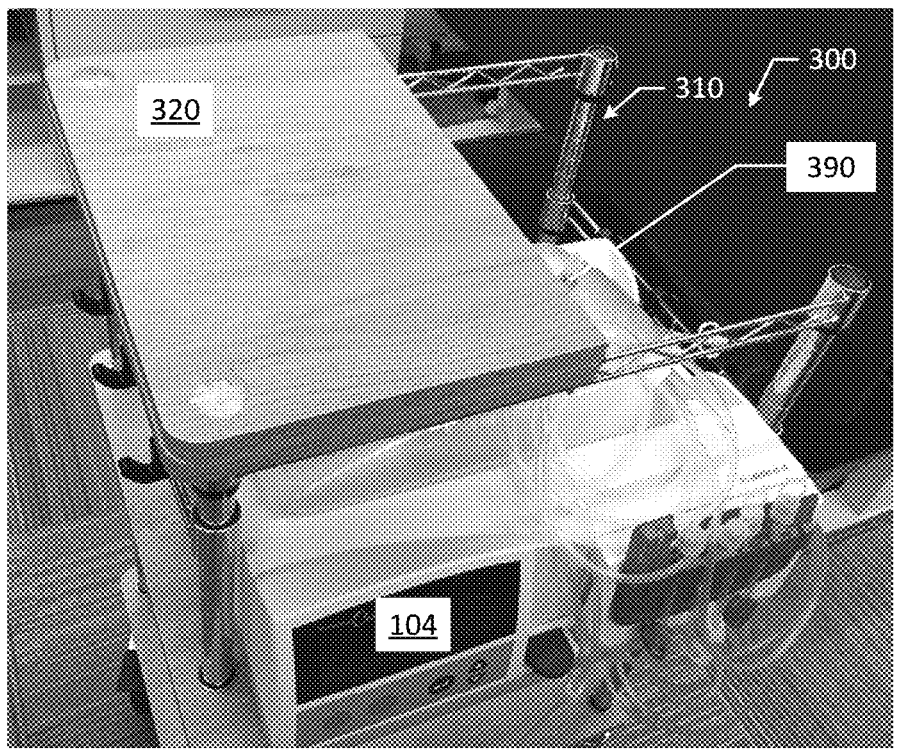
FIGS. 3E and 3F are top perspective views of the second embodiment for the mobile cart of the present disclosure.
Figure 3F:
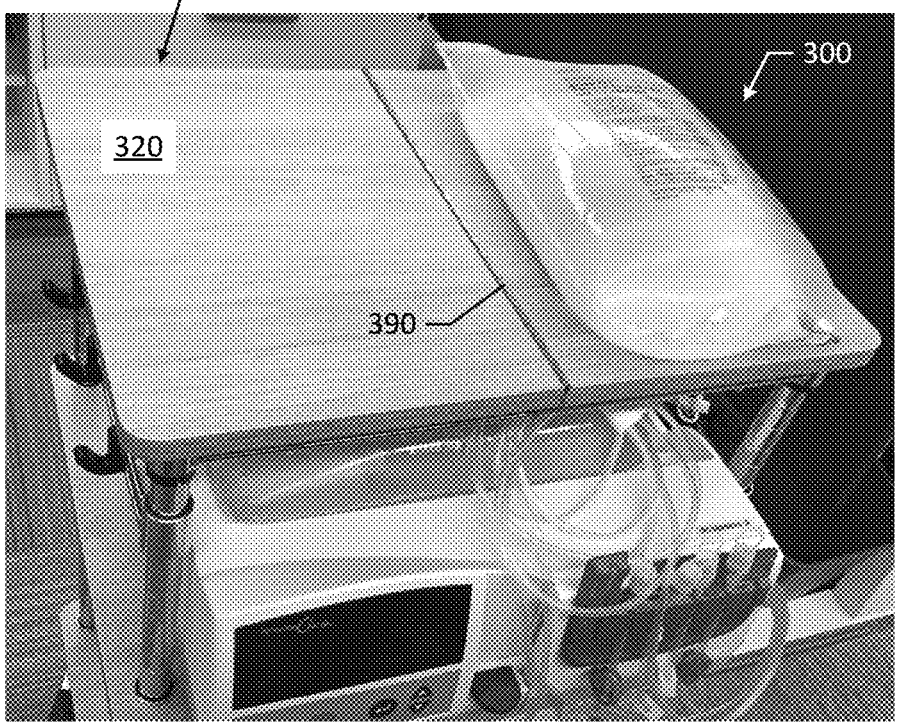

As illustrated in FIGS. 3E and 3F, top shelf 320 of cart 310 (and similarly top shelf 220 of cart 210) provides a work surface for the patient to initially organize and connect fluid bags. In some instances, cycler 104 may be positioned on top shelf 320. However, by providing a cycler compartment 230 (see FIGS. 2A to 2C) or a cycler compartment or shelf 330, the top shelf 320 is advantageously available as a work surface. Top shelf 320 in the illustrated embodiment includes a hinge 390 such that top shelf 320 may fold to open upwardly to provide direct access to heating tray 106. For example, hinge 390 on top shelf 320 may form a hinged top surface. FIG. 3G for example illustrates top shelf 320 in a folded configuration in which half of shelf 320 is folded about hinge 390 so as to lay upon the other half of the shelf. Doing so provides additional access to heating tray 106 and cycler 104 in general as well as to fluid bags 120a (e.g., dialysis solution and/or heating bag) located on heating tray 106. Hinge 390 is accordingly located along the middle As illustrated in FIGS. 3A, 3B and 3D, cycler compartment or shelf 330 may include a protruding portion 334 that extends beyond other shelves 320, 340 to allow space for tube routing from the cycler 104 (e.g., cassette) to various solution bags arranged on hooks 340. Additionally, protruding portion 334 may allow the cycler 104 to sit closer to the edge of the cart 310 and provide easier access and visibility to the controls and display of the cycler 104.

Similar to hooks 340, each compartment or shelf 330, 350 may also be adjustable to accommodate different types and models of cycler 104, different sizes and styles of fluid bags, and different drain configurations. Additionally, the overall height of carts 210 and 310 may also be adjustable. For example, a patient may adjust the height of cart 210, 310 based on the patient's bed height. Adjustment may be via the extension and contraction of the vertical posts of the cart 310, via adjustments made at wheels 280a to 280d or wheels 380a to 380d, and/or via adjustment to the height of Compartments 230, 240, 250 for cart 210.

Similar to hooks 340, cart 310 (and cart 210) may also include a holster (not shown) to hold hand sanitizer. Providing easy access to hand sanitizer minimizes the risk of contaminating the various components required to perform an APD therapy. For example, a patient may use the hand sanitizer prior to connecting solution bags to control possible bacterial contamination introduced while connecting solution bags. The sanitizer holster may be positioned in different locations about carts 210, 310 similar to hooks 340, which provides an easily accessible location for hand sanitizer, and wherein the patient does not need to open or close any of the compartments for access to the hand sanitizer.

Other holsters or compartments may additionally be positioned about carts 210, 310 for other components (e.g., consumables) such as gloves, caps, gauze, masks, tape, waste, etc.

Overall, the construction of carts 210, 310 is highly configurable to enable optimal use in a wide variety of different bedroom environments. In addition to the overall height of the carts 210, 310, the relative position of each compartment or shelf may also be adjustable. For example, the position of each shelf may be adjustable to accommodate different types and sizes of components and cyclers 104. Additionally, as discussed above, shelf height or overall cart height is adjustable in various embodiment to improve ease of use for patients of different heights and to adapt the cart according to the patient's bed height.

Figure 4:
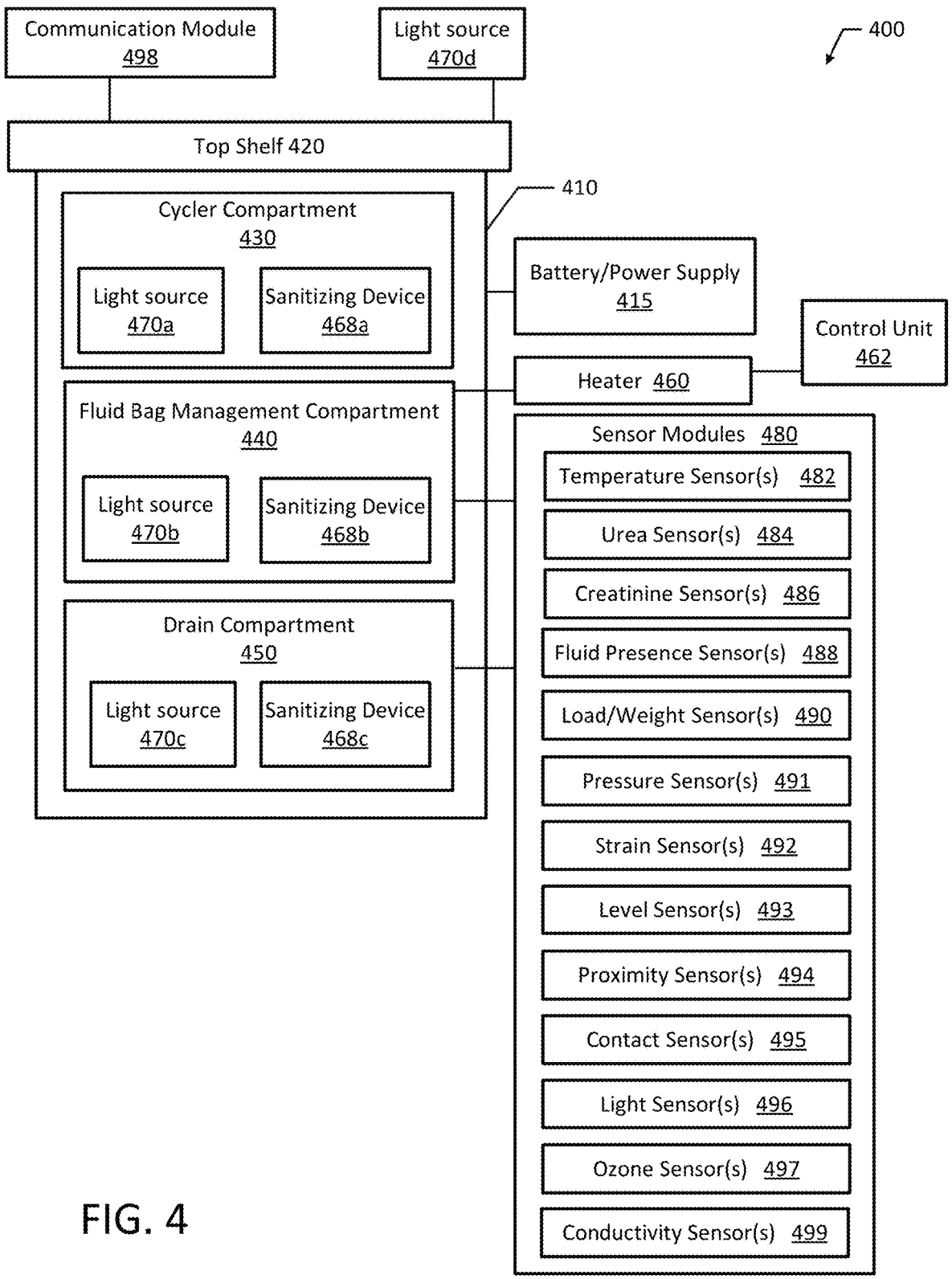
FIG. 4 is a schematic diagram of a mobile cart of the present disclosure.

FIG. 4 is a schematic view of another cart 410 of the present disclosure. It should be appreciated that all components, features, functionality and alternatives discussed in connection with carts 210 and 310 is also applicable to cart 410 and vice versa. For example, a feature described in relation to cart 310 (e.g., hooks 340) is similarly applicable to and/or combinable with carts 210, 410, such that those carts also embody that feature. The same applies for any feature of carts 210 and 410 being applicable to and/or combinable with the other carts. It should also be appreciated that different components of each of carts 210, 310 and 410 may be made of any combination of metal, plastic or wood. If metal, the component may for example be aluminum, steel or stainless steel. If plastic, the component may for example be polyvinyl chloride ("PVC"), polyethylene ("PE"), polyurethane ("PU") and/or polycarbonate.

As illustrated in FIG. 4, system 400 includes a cart 410, which allows the system 400 to be moved readily from one location to another. The cart 410 may be a mobile cart, and/or a multi-function cart, and/or a medical therapy cart, such as a dialysis therapy cart. The cart 410 includes a top shelf 420, a cycler compartment 430, a fluid bag management compartment 440, and a drain compartment 450. Top shelf 420, cycler compartment 430, fluid bag management compartment 440, and drain compartment 450 may include the same or similar features as the respective compartments and shelves described in connection with the carts 210, 310.

The cart 410 in the illustrated embodiment includes a battery or power supply 415, a heater or heating compartment 460, sanitizing, e.g., ultraviolet ("UV") light source(s) 470a to 470d configured and positioned and arranged to disinfect desired surfaces and chambers or cart 410. The cart 410 also includes sensor module 480, which may include one or more temperature sensor(s) 482, urea sensor(s) 484, creatinine sensor(s) 486, conductivity sensor(s) 499 and fluid presence sensor(s) 488. Temperature sensor(s) 482 are used in connection with onboard heating, while urea sensor(s) 484, creatinine sensor(s) 486, conductivity sensor(s) 499 and fluid presence sensor(s) 488 are used in connection with dialysis fluid sensing. For example, the conductivity sensor(s) 499 may sodium concentration information measured by the conductivity sensor(s) 499, which may provide information related to clearance. In an example, the conductivity sensor(s) 499 may be a sodium concentration sensor.

Cart 410 may implement shelves, compartments, trays, surfaces or hooks. For example, instead of a cycler compartment 230, cart 410 may instead include a cycler shelf. Furthermore, instead of fluid bag management compartment 240, cart 410 may instead include a fluid bag management shelf, a fluid bag management tray, or fluid bag hooks. Additionally, top shelf 220 may instead be a top surface, a top tray or a top compartment. In another example, instead of drain compartment 450, cart 410 may include a drain shelf or a drain hook to hold the drain bag 140. It should be appreciated that for each of the carts 210, 310, 410 discussed herein, each of the support structures may be in the form of shelves, compartments, trays, surfaces or hooks.

Any of the carts 210, 310 and 410 may include a handle (not pictured) to assist a patient in pushing or pulling the cart. As discussed in more detail below, the cart 210, 310, 410 may be configured to have an auto-adjustable height, shelf height, or compartment height to improve the layout of the cart for a specific application. For example, the overall cart height and various shelf or compartment heights may be adjusted based on a patient's bed height, a patient's reach, or a patient's height to provide optimum functionality including improved sightlines and instrument positioning. Additionally, the auto-adjustment or auto-leveling may ensure that the shelves or compartments provide a substantially horizontal support surface during use. The auto-adjustment or auto-leveling may be performed by leveling screws and an electric motor powered by a battery (e.g., onboard battery) or power supply 415.

The battery or power supply 415 may also provide power-assist to the wheels when the patient is pulling or pushing the cart. For example, the handle (not pictured) may include a power-assist button or switch, similar to that of a self-propelled vacuum or self-propelled electric lawn mower, which the patient may actuate to provide power to rotate the wheels while moving the cart.

Onboard Heater

It should be appreciated that carts 210, 310 and 410 are not limited to storing and operating with any particular type of cycler, including cycler 104. To that end, it is not required that the cycler operating with carts 210, 310 and 410 provide heating tray 106. It is contemplated to instead provide a more compact and simplified cycler, which does not heat the dialysis fluid. In such a situation, and even in the case that the cycler provides a heater, it is contemplated that any of carts 210, 310, 410 (here illustrated with cart 410) provide a heater 460 (e.g., onboard heater), such as a heating compartment to heat fluid bags. In various examples, heater 460 is implemented as an entire compartment or shelf dedicated to heating of the fluid bags, such as dialysis solution bags 120. Heater 460 is associated with the fluid bag management compartment or shelf. By dedicating a compartment or shelf for heating fluid bags 120 (e.g., dialysis solution bags), each of the fluid bags 120 can be efficiently heated at the same time. Additionally, the heating portion of carts 210, 310, 410 may keep each of the fluid bags 120 warm such that they are constantly ready for use.

In an example, heater 460 may be a thermostatic device integrated in one or more of a rear panel, a side panel, a top or a bottom of the fluid bag management compartment or shelves of the cart 210, 310, 410. In various examples, the heater 460 may be a resistive plate heater or include multiple resistive heaters, e.g., a resistive heater for each fluid bag 120. In an alternative embodiment, carts 210, 310, 410 may be equipped with a heating blanket that can be placed around fluid bags. Additionally or alternatively, a heating sleeve may be placed over one or more of the solution bags to heat the solution while the one or more bag sits in fluid bag management compartment or shelves or hangs from hooks 340. Radiant heating may also be used alone or in addition to resistive heating. In other examples, the heater 460 may be adapted for inductive heating, micro-wave heating or the like.

Incorporating a thermostatic device within carts 210, 310, 410 allows multiple fluid bags 120 to be heated and kept warm at the same time, which avoids the need to lift a fluid bag 120a (e.g., heating bag) onto the heater tray 106. Both heating and maintaining the heat of multiple fluid bags 120 also reduce set-up time between treatments. To further reduce set-up for treatment time, the treatment time may be further optimized by heating the fluid bags 120 prior to the treatment by means of a timer function. The heater 460, such as a thermostatic device, may include a plurality of heating coils that are embedded within the compartment or below the shelf surface. Carts 210, 310, 410 in the illustrated embodiment include one or more temperature sensor 482 positioned on or within the heated surface to track the temperature of the solution in the fluid bags 120. For example, temperature sensor(s) 482 may provide feedback to a control unit 462 for heater 460, which includes a control circuit that turns heater 460 on and off as needed to maintain the dialysis fluid at the desired temperature.

In an embodiment, fluid bag management compartment having onboard heater 460 is insulated, e.g., includes insulated sides, rear panel, top and bottom and perhaps the door. The insulation increases the efficiency of the fluid bag management compartment that is heated by heater 460. Each of the heaters 460 described herein, such as the heating tray 106, heating compartment, heating shelf, onboard heater, resistive plate heater, heating blanket, heating sleeve, infrared heater, inductive heater, micro-wave heater etc., may be referred to generally as a heating device 460.

Light Sanitization

Carts 210, 310, 410 may include one or more sanitizing device 468a to 468c configured to sanitize shelves, compartments, or components housed on or within the carts, such as the sanitizing of specific location(s) of a disposable set associated with the fluid bags. The sanitizing devices 468a to 468c may be generally referred to as sanitizing device(s) 468. The sanitizing devices 468 may be light sources 470a to 470d that emit light capable of sterilization or disinfection. In addition to the holster providing hand sanitizer, light source(s) 470a to 470d, hereinafter referred to generally as light source(s) 470, are configured to emit sanitizing, e.g., UV light capable of sterilization or disinfection to further control possible bacterial contaminations introduced to the various therapy components (e.g., when connection solution bags). For example, light source(s) 470 may be positioned and arranged to illuminate the solution bag connectors in the fluid bag management compartments 240, 440 and a similar compartment in cart 310.

Light source 470 may be an ultraviolet ("UV") light source, such as UV bactericidal lights. In other examples, the light source 470 may be a mercury vapor lamp, a xenon flash lamp, a continuous arc lamp, and may include multiple UV light emitting diodes (LEDs), etc. Light source 470 may emit UVA, UVB, or UVC light. Additionally, light source 470 may emit both UV and visible light. By emitting UV light from different portions of the electromagnetic spectrum, carts 210, 310 and 410 may be more effective at sanitizing APD components over a broader range of microorganisms.

Light may be emitted from light sources 470 so as to provide continuous sterilizing radiation over a period of time. Alternatively, light is emitted in pulses or flashes at selected times and at predetermined intervals. In an example, the energy of a single pulse may be sufficient to deliver a sanitizing or disinfecting dosage to the APD components within the compartment, e.g., connector locations or areas of fluid bags 120. To that end, light sources 470 are positioned and aimed to direct sanitizing light towards the desired locations and areas of the solution bags or other desired location of disposable set 118. The light sources 470 may for example be mounted to the sides, tops or rear surfaces of carts 210, 310 or 410 and/or to a frame of the carts.

Each compartment or shelf may be associated with its own light source 470 (e.g., disinfecting light source or sanitizing light source). In the example illustrated in FIG. 4, cycler compartment 430 is associated with light source 470a, fluid bag management compartment 440 is associated with light source 470b, while drain compartment 450 is associated with light source 470c. Additionally, top shelf 420 may be associated with light source 470d. Any of light sources 470a to 470d may be a light provided on the end of a flexible "snake" type connection, or a universal hinge type connection, which can be pointed at different regions of, e.g., the top shelf 420, to provide "spot" sanitization. The intensity, treatment period, quantity or frequency of pulses, etc., of the light emitted by light sources 470 may be adjusted for each compartment or shelf. For example, the compartments or shelves may house components made of different materials that may require different treatment parameters for sterilization or disinfection. Additionally, the compartments or shelves along with the components housed within those compartments or shelves may be designed such that the sanitizing light (e.g., UV light) does not damage or deteriorate the compartments, shelves or components housed within the compartments or shelves. For example, the compartments, shelves and/or components may made from UV-resistant materials.

The light sources, which may emit sanitizing light such as UV light, advantageously help to maintain sterility and reduce the threat of contamination to the patient. Sanitizing components via light source(s) 470 may reduce the risk of peritonitis. Each shelf, compartment, tray or hook may be protected with light opaque materials that minimize UV light or other light from exiting the enclosure, thereby minimizing the exposure to patients and other bystanders. Therefore, the patient may safely and comfortably use cart(s) 210, 320, 410 without unwanted exposure to UV light or other light, especially during night use.

Ozone Sanitization

The carts 210, 310, 410 may alternatively or additionally perform sanitization and/or sterilization using ozone containing gas. For example, the carts may include one or more sanitizing devices 468 configured to sanitize shelves, compartments, or components housed on or within the carts, such as sanitizing specific location(s) of a disposable set associated with the fluid bags. The sanitizing device 468 configured to sanitize may include an ozone generator. The sanitizing device 468 may also include other components associated with ozone generator, which are discussed in more detail below. The ozone may be produced externally and then supplied to one or more compartments of the carts 210, 310, 410. In an example, medical quality oxygen is converted into ozone containing gas in an ozone generator. The oxygen may be supplied from a supply tank. Additionally, the ozone containing gas may be stored in a storage tank. The ozone generator may be housed on or housed within the cart 210, 310, 410. Similarly, the oxygen supply tank and storage tank may be housed on or within the cart. In another example, the ozone generator, oxygen supply tank, and storage tank may be located external to the cart. The cart 210, 310, 410 may also include a vacuum pump associated with the compartments to provide a sufficient vacuum to the compartment to increase the penetration of the ozone gas.

The medical quality oxygen may pass through a filter before being converted into ozone containing gas. Additionally, the ozone containing gas may pass from the supply tank, through a filter, a pressure regulator, a flow meter and/or shut-off valve before entering one of the cart's compartments. For example, the ozone containing gas may be directed to one of the cart's compartments through a flow regulator or pressure regulator. The carts 210, 310, 410 and any associated compartments may include covers or seals (e.g., gasket seals) for each compartment to ensure the ozone containing gas is retained in a target compartment to perform sanitization or sterilization.

Sensors

Carts 210, 310, 410 may include a desired sensor module 480. As discussed above, carts 210, 310, 410 may include temperature sensors 482 positioned on or within the compartments having onboard heated surfaces to track the temperature of solution within fluid bags 120. As discussed above, temperature sensor(s) 482 may be used as feedback to a control unit 462 of heater or heating device 460 (e.g., onboard heater), which turns heater 460 on and off as needed to maintain dialysis fluid at a desired temperature, e.g., body temperature of 37° C.

FIG. 4 illustrates that urea, creatinine and/or turbidity sensors 484, 486 may be employed so as to sense the patient's drain fluid or effluent, e.g., be incorporated into the drain bag 140 or along its associated drain line to sense one or more fluid properties of the effluent in the drain bag 140. Additionally, conductivity sensors 499 may provide conductivity information or sodium concentration information of the fluid. For example, the sensors may be used to identify substances (e.g., urea and creatinine) as well as the concentration of such substances, which provides information regarding the composition of the solution in the drain bag 140. The sensors may alternatively or additionally look for white cells as an indicator of peritonitis. Sensors 484, 486 and/or 488 may be optical and/or inductive or capacitive sensors. Other sensors (not pictured) may include and effluent sensor, however in some examples, the effluent sensor may generally refer to any one of the urea sensors 484, creatinine sensors 486 or turbidity sensors.

Each of the compartments, shelves, surfaces or trays of carts 210, 310 and 410 may also include leakage sensors or fluid presence sensors 488. For example, the leakage sensors or fluid presence sensors 488, e.g., electrical contacts, may detect the presence of a fluid's leakage within a compartment or on a shelf surface (e.g., fluid that is leaking from a bag or a connection line). Leakage sensors or fluid presence sensors 488 advantageously provide early detection and warnings to the patient if a fluid bag is leaking or if a bag connector is not properly attached. Sensors 484, 486 and 488, in an embodiment, output to a control unit, such as the same control unit 462 for the heater 460. The sensors may provide system and patient data that can be delivered to a desired location and/or output to an alarm, e.g., audio, visual or audiovisual alarm.

Additionally, each of the compartments, shelves, surfaces, trays or hook of carts 210, 310 and 410 may also include a load or weight sensor(s) 490, a pressure sensor(s) 491, a strain sensor(s) 492, a level sensor(s) 493, or any combination thereof. For example, the outputs of any of the load or weight sensors 490, pressure sensors 491, strain sensors 492 or level sensors 493 may be used to provide volume or flowrate monitoring and control both to and from the patient. The sensors may measure an infused mass, an infused volume, a drained mass, or a drained volume to or from the patient. Measurements may be obtained in compartments, shelves, surfaces, trays in which sanitization or disinfection is taking place (e.g., sanitizing connectors). Additionally, measurements may be obtained in compartments, shelves, surfaces, trays in which heating is taking place (e.g., heating fluid bags 120). In an example, the load or weight sensor(s) 490, pressure sensor(s) 491 and/or strain sensor(s) 492 may be positioned on or be integrated with hooks 340. In an example, the weight sensor(s) 492 may be a scale or form part of a scale. It should be appreciated that the load or weight sensor(s) 490 may be either a load sensor or a weight sensor. Additionally, the load or weight sensor(s) 490 may include a combination of load sensors and weight sensors.

The level sensor(s) 493 may also be used to monitor the orientation of the cart 210, 310, 410. For example, level sensor(s) 493 may be used to ensure that the cart is in a horizontal orientation, for example, that each compartment, shelf or tray provides a support surface that resides in a substantially horizontal plane. As noted above, each shelf, compartment or tray may be adjustable and the overall height of carts 210, 310 and 410 may be adjustable. Adjustment may be via the extension and contraction of the vertical posts of cart 210, 310, 410 via adjustments made at wheels 280a to 280d or wheels 380a to 380d, and/or via adjustment to the height of compartments (e.g., compartments 230, 240, 250) and or shelves. The cart 210, 310, 410 may be configured for auto-adjustment or auto-leveling. In other examples, the cart 210, 310, 410 may be manually adjusted with adjustment screws located in each of the vertical posts. Depending on the reading from level sensor(s), adjustments may be made to the shelves, the compartments or to the cart in general to position each shelf or compartment in a substantially horizontal orientation when the cart is positioned on an uneven or non-level surface. Properly adjusting the cart, shelves or compartments such that the fluid bags are supported by or on a substantially horizontal surface may improve the accuracy of measurements or readings from level sensor(s) used to determine the mass or volume of fluid in fluid bags or containers.

FIG. 4 also illustrates that proximity sensor(s) 494 or contact sensor(s) 495 may be employed to determine the presence of fluid bags 120, drain bags 140, tubing and/or connectors. In an example, the proximity sensors 494 and/or the contact sensors 495 may be used in combination with light sensor(s) 496 or ozone sensor(s) 497 to ensure that sanitizing devices 468 (e.g., UV lights or ozone generator) are activated when an object to be sanitized (e.g., a fluid bag 120 or connector) is present. Otherwise, the sanitizing devices 468 may be deactivated (or not be activated) if an object to be sanitized is not detected.

Just-In-Time Ordering

Carts 210, 310 and 410 may include a communication module 498 that is communicatively connected to a network (e.g., wired or wireless network). Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology. Based on information obtained from load or weight sensor(s) 490, a pressure sensor(s) 491, a strain sensor(s) 492, a level sensor(s) 493, etc., the cart may be configured to order consumables such as fluid bags 120 (e.g., dialysis fluid bags), drain bags 140, and connectors. The just-in-time ordering functionality of carts 210, 310 and 410 may continually update delivery schedules based on the sensor information. It should be appreciated that fluid bags, drain bags and connectors are a few examples of consumables that me be ordered over connection established between the cart and the network. These examples are provided for illustrative purposes and are non-limiting. For example, the communication module 498 may be used to order other consumables needed by the patient.

Optimized PD

Carts 210, 310 and 410 enable the performance of an "optimized PD" therapy in which different PD dialysis fluids are used to provide an optimized physiological treatment tailored for the patient. An "optimized PD" may include, for example, alternating dwell cycles between a high glucose solution and a no (or low) glucose solution. By performing fluid heating in a compartment or shelf of the cart 210, 310, 410, such that all bags are heated at the same time, cycler 104 can draw from any of the, e.g., three fluid bags 120a to 120c (e.g., dialysis solution bags) during a given fill cycle and can offer the ability to tailor the solution composition per fill cycle.

Conversely, other systems and "ad hoc" arrangements may require that the first fluid bag 120a (e.g., dialysis solution bag) is placed on the heating tray 106 of the cycler 104 thus limiting which solution bags the cycler 104 can pull solution from and thus limits the type of APD therapy the can be performed.

It should be understood that various changes and modifications to the presently preferred embodiments described herein will be apparent to those skilled in the art. It is therefore intended that such changes and modifications are covered by the appended claims.

The invention is claimed as follows:

1. A mobile dialysis therapy cart comprising:
   a top shelf;
   a cycler compartment positioned below the top shelf, the cycler compartment sized and shaped to house an automated peritoneal dialysis ("APD") cycler;
   a fluid bag management compartment sized and shaped to house at least two fluid bags, the fluid bag management compartment positioned below the cycler compartment and including a heating device adapted to heat dialysis fluid in one or more of the at least two fluid bags;
   a drain compartment positioned below the fluid bag management compartment; and
   a plurality of wheels.

2. The mobile dialysis therapy cart of claim 1, further comprising at least one sanitizing device configured to sanitize at least one location of a disposable set associated with the at least two fluid bags.

3. The mobile dialysis therapy cart of claim 2, wherein the at least one sanitizing device includes a sanitizing light source directed towards the at least one location.

4. The mobile dialysis therapy cart of claim 2, wherein the at least one sanitizing device includes an ozone generator configured to direct ozone containing gas towards the at least one location.

5. The mobile dialysis therapy cart of claim 1, wherein the heating device includes at least one of a resistive plate heater, an inductive heater, and a micro-wave heater.

6. The mobile dialysis therapy cart of claim 1, wherein the top shelf includes a hinge configured to enable a portion of the top shelf to rotate upwards to provide access to the cycler compartment.

7. The mobile dialysis therapy cart of claim 1, further comprising a drain trolley housed within the drain compartment, wherein the drain compartment includes a ramp for the drain trolley.

8. The mobile dialysis therapy cart of claim 1, wherein the fluid bag management compartment includes at least two telescoping sub-shelves configured to collapse.

9. The mobile dialysis therapy cart of claim 1, further comprising at least one of a urea sensor, a creatinine sensor, a conductivity sensor, a turbidity sensor for sensing patient effluent, or a fluid presence sensor for detecting a leak in the fluid bag management compartment.

10. The mobile dialysis therapy cart of claim 1, further comprising at least one of a pressure sensor, a contact sensor, a load or weight sensor, or a strain sensor for sensing a mass or volume of fluid that is delivered to or from a patient.

11. The mobile dialysis therapy cart of claim 1, further comprising a level sensor for sensing an orientation of the mobile dialysis therapy cart, the cycler compartment, the fluid bag management compartment, or the drain compartment.

12. The mobile dialysis therapy cart of claim 1, wherein the drain compartment includes at least one of a load or weight sensor, a pressure sensor, a contact sensor, a strain sensor, a urea sensor, a creatinine sensor, a turbidity sensor, or a proximity sensor.

13. A dialysis therapy system comprising:
   a cart including:
      a top shelf,
      a cycler compartment positioned below the top shelf,
      a fluid bag management compartment sized and shaped to house at least two fluid bags, the fluid bag management compartment positioned below the cycler compartment and including a heating device adapted to heat dialysis fluid in one or more of the at least two fluid bags, and
      a plurality of wheels; and
   an automated peritoneal dialysis ("APD") cycler housed within the cycler compartment, wherein the cycler compartment is sized and shaped to house the APD cycler.

14. The dialysis therapy system of claim 13, wherein the cart further includes a drain compartment positioned below the fluid bag management compartment.

15. The dialysis therapy system of claim 14, further comprising a drain bag, wherein the drain bag is housed within the drain compartment.

16. The dialysis therapy system of claim 15, further comprising at least one of a urea sensor, a creatinine sensor, and a turbidity sensor associated with the drain bag or the drain compartment.

17. The dialysis therapy system of claim 14, further comprising a sanitizing device configured to sanitize a portion of the dialysis therapy system.

18. The dialysis therapy system of claim 17, wherein the sanitizing device is at least one of a sanitizing light source or an ozone generator.

19. The dialysis therapy system of claim 14, further comprising at least one of a load or weight sensor, a pressure sensor, a strain sensor, and a level sensor.

* * * * *